US012508382B2

(12) United States Patent
Ward et al.

(10) Patent No.: US 12,508,382 B2
(45) Date of Patent: Dec. 30, 2025

(54) MYOFUNCTIONAL TRAINING WITH NEGATIVE AIRWAY PRESSURE FOR OBSTRUCTIVE SLEEP APNEA

(71) Applicant: University of Rochester, Rochester, NY (US)

(72) Inventors: Denham Ward, Pittsford, NY (US); Suzanne Karan, Rochester, NY (US)

(73) Assignee: University of Rochester, Rochester, NY (US)

( * ) Notice: Subject to any disclaimer, the term of this patent is extended or adjusted under 35 U.S.C. 154(b) by 826 days.

(21) Appl. No.: 17/843,039

(22) Filed: Jun. 17, 2022

(65) Prior Publication Data

US 2022/0401679 A1 Dec. 22, 2022

Related U.S. Application Data

(60) Provisional application No. 63/212,152, filed on Jun. 18, 2021.

(51) Int. Cl.
*A61M 16/06* (2006.01)
*A61M 16/00* (2006.01)

(52) U.S. Cl.
CPC . *A61M 16/0605* (2014.02); *A61M 2016/0018* (2013.01); *A61M 2016/0027* (2013.01)

(58) Field of Classification Search
CPC .......... A61M 16/0009; A61M 16/0605; A61M 2016/0018; A61M 2016/0027; A61M 16/06; A61M 16/024; A61M 2205/505; A61M 16/0003; A61M 2016/003; A61B 5/08; A61B 5/087; A61B 5/14542; A61B 5/369; A61B 5/389; A61B 5/398; A61B 5/0826; A61B 5/4818; A61B 5/4836
See application file for complete search history.

(56) References Cited

U.S. PATENT DOCUMENTS

| | | | |
|---|---|---|---|
| 7,918,222 | B2 | 4/2011 | Chen |
| 8,074,656 | B2 | 12/2011 | Vaska |
| 8,122,889 | B2 | 2/2012 | Vaska |
| 8,122,890 | B2 | 2/2012 | Vaska |
| 8,387,620 | B1 | 3/2013 | Vaska |
| 8,402,973 | B2 | 3/2013 | Podmore |
| 8,505,540 | B2 | 8/2013 | Vaska |
| 8,567,406 | B2 | 10/2013 | Chen |
| 8,573,223 | B2 | 11/2013 | Podmore |
| 8,616,208 | B2 | 12/2013 | Chen |
| 8,656,922 | B2 | 2/2014 | Vaska |

(Continued)

FOREIGN PATENT DOCUMENTS

EP 2943170 11/2015

OTHER PUBLICATIONS

Bird SP, Tarpenning KM, Marino FE. Designing resistance training programmes to enhance muscular fitness: a review of the acute programme variables. Sports Med 2005; 35: 841-851.

(Continued)

*Primary Examiner* — Valerie L Woodward
(74) *Attorney, Agent, or Firm* — Riverside Law LLP

(57) ABSTRACT

The present invention provides a method and apparatus for treating a subject suffering from obstructive sleep apnea (OSA). In one embodiment, the method of the present invention is configured to deliver negative airway pressure to a subject's airway to strengthen the airway muscle tone.

11 Claims, 4 Drawing Sheets

(56) References Cited

U.S. PATENT DOCUMENTS

| | | | |
|---|---|---|---|
| 8,667,970 B2 | 3/2014 | Podmore | |
| 8,701,672 B2 | 4/2014 | Vaska | |
| 8,979,823 B2 | 3/2015 | Podmore | |
| 9,101,495 B2 | 8/2015 | Mcanelly | |
| 9,138,342 B2 | 9/2015 | Chen | |
| 9,241,825 B2 | 1/2016 | Vaska | |
| 9,339,620 B2 | 5/2016 | Chen | |
| 9,375,541 B2 | 6/2016 | Vitale | |
| 9,387,117 B2 | 7/2016 | Chen | |
| 9,387,118 B2 | 7/2016 | Vaska | |
| 9,387,119 B2 | 7/2016 | Podmore | |
| 9,483,792 B2 | 11/2016 | Podmore | |
| 9,549,795 B2 | 1/2017 | Podmore | |
| 9,610,190 B2 | 4/2017 | Vaska | |
| 9,655,768 B2 | 5/2017 | Vaska | |
| 9,763,759 B2 | 9/2017 | Vitale | |
| 10,080,855 B2 | 9/2018 | Chen | |
| 10,117,773 B2 | 11/2018 | Podmore | |
| 10,149,782 B2 | 12/2018 | Chen | |
| 10,149,783 B2 | 12/2018 | Chen | |
| 10,159,595 B2 | 12/2018 | Chen | |
| 10,166,140 B2 | 1/2019 | Chen | |
| 10,245,175 B2 | 4/2019 | Podmore | |
| D871,571 S | 12/2019 | Chen | |
| 2002/0023644 A1* | 2/2002 | Berthon-Jones | A61B 5/085 128/204.22 |
| 2004/0200474 A1* | 10/2004 | Lurie | A61M 16/0825 128/203.11 |
| 2010/0147302 A1* | 6/2010 | Selvarajan | A61M 16/0622 128/205.24 |
| 2011/0192404 A1* | 8/2011 | Chen | A61M 16/0488 128/848 |
| 2019/0192797 A1* | 6/2019 | Martin | A61M 16/0057 |

OTHER PUBLICATIONS

Catlin G. Shut Your Mouth and Save Your Life. Fourth ed. Paternoster Row: N. Truebner & Co.; 1870 (pp. 1-119).

Clark HM. Neuromuscular treatments for speech and swallowing: a tutorial. Am J Speech Lang Pathol 2003; 12: 400-415.

De Felicio CM, da Silva Dias FV, Trawitzki LVV. Obstructive sleep apnea: focus on myofunctional therapy. Nat Sci Sleep 2018; 10: 271-286.

Diaferia G, Santos-Silva R, Truksinas E, Haddad FLM, Santos R, Bommarito S, Gregorio LC, Tufik S, Bittencourt L. Myofunctional therapy improves adherence to continuous positive airway pressure treatment. Sleep Breath 2017; 21: 387-395.

Eckert DJ, White DP, Jordan AS, Malhotra A, Wellman A. Defining phenotypic causes of obstructive sleep apnea. Identification of novel therapeutic targets. Am J Respir Crit Care Med 2013; 188: 996-1004.

Guimaraes KC, Drager LF, Genta PR, Marcondes BF, Lorenzi-Filho G. Effects of oropharyngeal exercises on patients with moderate obstructive sleep apnea syndrome. Am J Respir Crit Care Med 2009; 179: 962-966.

Holty JE, Guilleminault C. Surgical options for the treatment of obstructive sleep apnea. Med Clin North Am 2010; 94: 479-515.

Hsu B, Emperumal CP, Grbach VX, Padilla M, Enciso R. Effects of respiratory muscle therapy on obstructive sleep apnea: a systematic review and meta-analysis. J Clin Sleep Med 2020; 16: 785-801.

Kezirian EJ. Nonresponders to pharyngeal surgery for obstructive sleep apnea: insights from drug-induced sleep endoscopy. Laryngoscope 2011; 121: 1320- 1326.

Lequeux T, Chantrain G, Bonnand M, Chelle AJ, Thill MP. Physiotherapy in obstructive sleep apnea syndrome: preliminary results. Eur Arch Otorhinolaryngol 2005; 262: 501-503.

Litman RS, Hayes JL, Basco MG, Schwartz AR, Bailey PL, Ward DS. Use of dynamic negative airway pressure (DNAP) to assess sedative-induced upper airway obstruction. Anesthesiology 2002; 96: 342-345.

Mann EA, Burnett T, Cornell S, Ludlow CL. The effect of neuromuscular stimulation of the genioglossus on the hypopharyngeal airway. Laryngoscope 2002; 112: 351-356.

Mediano O, Romero-Peralta S, Resano P, Cano-Pumarega I, Sanchez-de-la-Torre M, Castillo-Garcia M, Martinez-Sanchez AB, Ortigado A, Garcia-Rio F. Obstructive Sleep Apnea: Emerging Treatments Targeting the Genioglossus Muscle. J Clin Med 2019; 8 (pp. 1-18).

Neumannova K, Hobzova M, Sova M, Prasko J. Pulmonary rehabilitation and oropharyngeal exercises as an adjunct therapy in obstructive sleep apnea: a randomized controlled trial. Sleep Med 2018; 52: 92-97.

Norton JR, Ward DS, Karan S, Voter WA, Palmer L, Varlese A, Rackovsky O, Bailey P. Differences between midazolam and propofol sedation on upper airway collapsibility using dynamic negative airway pressure. Anesthesiology 2006; 104: 1155-1164.

Puhan MA, Suarez A, Lo Cascio C, Zahn A, Heitz M, Braendli O. Didgeridoo playing as alternative treatment for obstructive sleep apnoea syndrome: randomised controlled trial. BMJ 2006; 332: 266-270.

Series F, Cote C, Simoneau JA, St Pierre S, Marc I. Upper airway collapsibility, and contractile and metabolic characteristics of musculus uvulae. FASEB J 1996; 10: 897-904. 16.

Smith PL, Eisele DW, Podszus T, Penzel T, Grote L, Peter JH, Schwartz AR. Electrical stimulation of upper airway musculature. Sleep 1996; 19: S284-287.

Suratt PM, Wilhoit SC, Cooper K. Induction of airway collapse with subatmospheric pressure in awake patients with sleep apnea. J Appl Physiol Respir Environ Exerc Physiol 1984; 57: 140-146.

Suzanne Karan, William A. Voter, Denham Ward (2021) Myofunctional training with negative airway pressure for obstructive sleep apnea: a prospective non-randomized cohort feasibility study. F1000Research 2021, 10:1092 (pp. 1-13).

Suzuki H, Watanabe A, Akihiro Y, Takao M, Ikematsu T, Kimoto S, Asano T, Kawara M. Pilot study to assess the potential of oral myofunctional therapy for improving respiration during sleep. J Prosthodont Res 2013; 57: 195-199.

Trzepizur W, Cistulli PA, Glos M, Vielle B, Sutherland K, Wijkstra PJ, Hoekema A, Gagnadoux F. Health Outcomes of Continuous Positive Airway Pressure versus Mandibular Advancement Device for the Treatment of Severe Obstructive Sleep Apnea: an Individual Participant Data Meta-analysis. Sleep 2021 (pp. 1-8).

Verma RK, Johnson JJ, Goyal M, Banumathy N, Goswami U, Panda NK. Oropharyngeal exercises in the treatment of obstructive sleep apnoea: our experience. Sleep Breath 2016; 20: 1193-1201.

Weaver TE, Grunstein RR. Adherence to continuous positive airway pressure therapy: the challenge to effective treatment. Proc Am Thorac Soc 2008; 5: 173-178.

Website: Somnics Inc. https://somnics.com—May 16, 2021 (pp. 1-3).

Wheatley JR, Mezzanotte WS, Tangel DJ, White DP. Influence of sleep on genioglossus muscle activation by negative pressure in normal men. Am Rev Respir Dis 1993; 148: 597-605.

* cited by examiner

MYOFUNCTIONAL TRAINING WITH NEGATIVE AIRWAY PRESSURE FOR OBSTRUCTIVE SLEEP APNEA

CROSS REFERENCE TO RELATED APPLICATIONS

This application claims priority to U.S. Provisional Patent Application No. 63/212,152, filed Jun. 18, 2021, the contents of which are incorporated by reference herein in its entirety.

STATEMENT REGARDING FEDERALLY SPONSORED RESEARCH OR DEVELOPMENT

This invention was made with government support under RR024160 awarded by National Institutes of Health. The government has certain rights in the invention.

BACKGROUND OF THE INVENTION

Obstructive sleep apnea (OSA) is caused by upper airway collapse during sleep resulting in a disruption of regular periodic breathing. The phenotypes of OSA pathology are variable and a particular patient can have the disorder because of anatomical and/or non-anatomical reasons (Eckert, D. J. et al., 2013, Am J Respir Crit Care Med 188:996-1004). Continuous or auto-titrated positive airway pressure (PAP) is the current standard treatment; however, other therapies have emerged as alternatives. Mandibular advancement devices (or oral appliances) are currently recommended as a second line therapy (Trzepizur, W. et al., 2021, Sleep); though the ability to properly track compliance (and thus efficacy) is a challenge. Surgical interventions have targeted anatomical or morphological problems in those unresponsive to standard therapies. However, the evidence supporting its widespread application is lacking (Holty, J. E. et al., 2010, Med Clin North Am 94:479-515).

Thus, there is a need in the art for a method of providing negative airway 30 pressure therapy in awake subjects, to improve the signs and symptoms of this syndrome. The present invention meets this need.

SUMMARY OF THE INVENTION

In one aspect, the present invention provides a system comprising: a mask to be placed sealingly over a subject's face and thereby form a chamber between the mask and the subject's face, wherein the mask comprises an inlet port configured to receive a flow of breathable gas; and a pump attached to one end of the inlet port, wherein the pump is capable of creating a pressure of about −1 to −25 cm $H_2O$ in the chamber. In one embodiment, the mask is structured to cover the subject's nasal and oral region. In one embodiment, the mask further comprises a pneumotachograph to measure air flow within the chamber. In one embodiment, the mask further comprises a pressure transducer configured to measure the pressure in the mask.

In one aspect, the present invention provides a method for treating obstructive sleep apnea, comprising the steps of: measuring one-repetition maximum (1RM) of a subject; and providing negative airway pressure based on the measured 1RM to the subject. In one embodiment, the negative airway pressure is provided to the subject through a mask sealingly positioned on the subject's face. In one embodiment, the negative airway pressure is provided to the subject through a mouthpiece. In one embodiment, the negative airway pressure is configured to be approximately about −1 to −25 cm $H_2O$. In one embodiment, the negative airway pressure is provided for approximately 4-7 sets wherein in each set, the subject is exposed to the measured 1RM repetitiously for at least 1 breath. In one embodiment, the subject is exposed to the measured 1RM repetitiously for approximately 1-5 breaths in each set. In one embodiment, the subject is subjected to a rest time of at least 1 minutes between sets. In one embodiment, the 1RM is measured by exposing the subject to a variety of negative pressures. In one embodiment, the subject is exposed to the variety of negative pressures in an increasing-decreasing manner. In one embodiment, the subject is exposed to the variety of negative pressures in a random sequence.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

DETAILED DESCRIPTION

Figure 1:
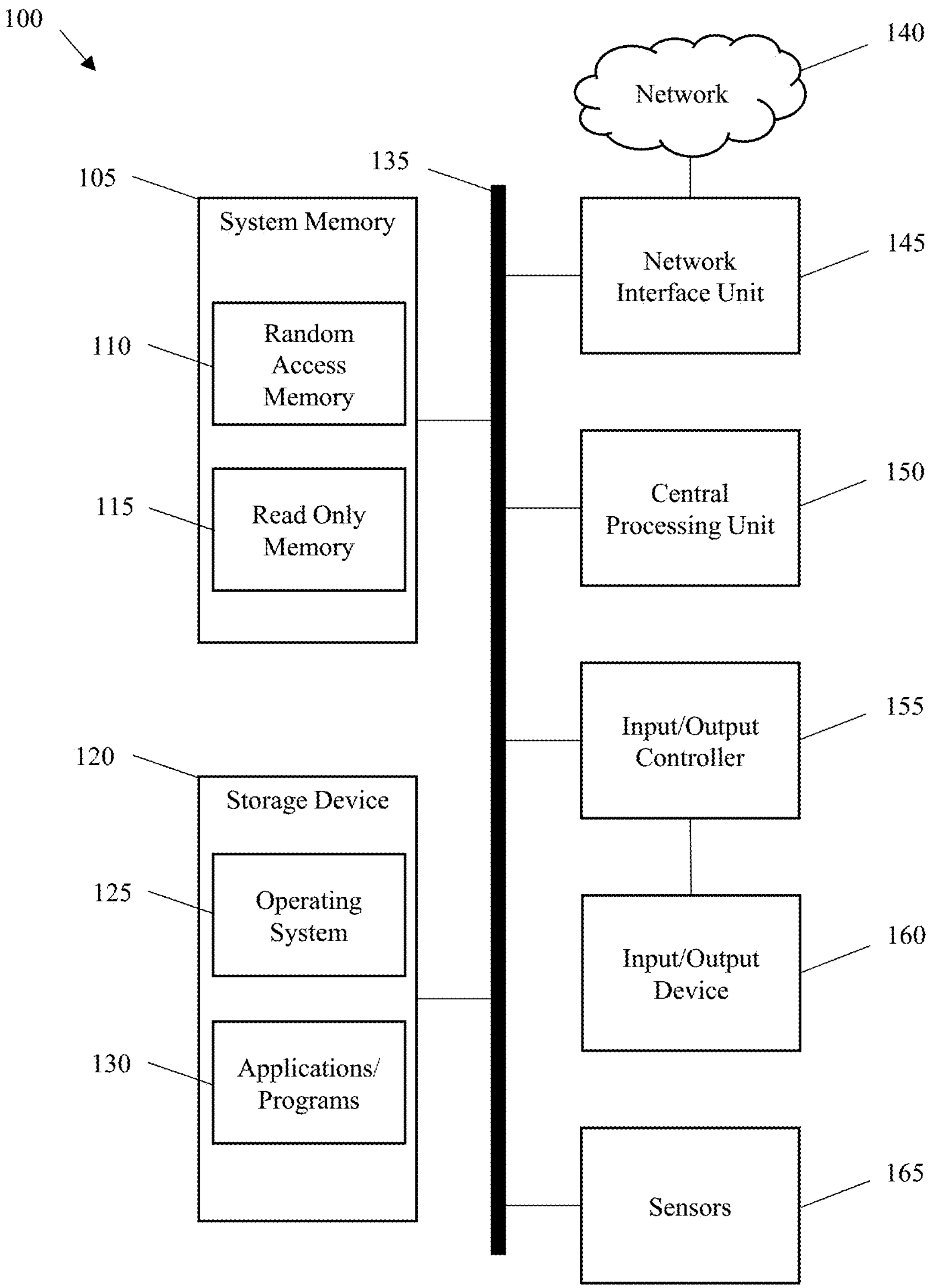
FIG. 1 is a diagram of a computing device.

It is to be understood that the figures and descriptions of the present invention have been simplified to illustrate elements that are relevant for a clear understanding of the present invention, while eliminating, for the purpose of clarity many other elements found in the field of obstructive sleep apnea. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, exemplary materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

The terms "patient," "subject," "individual," and the like are used interchangeably herein, and refer to any animal amenable to the systems, devices, and methods described herein. The patient, subject or individual may be a mammal, and in some instances, a human.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Parts of this invention may be described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention may be described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

FIG. 1 and the following discussion are intended to provide a brief, general description of a suitable computing environment in which aspects of the invention may be implemented. While the invention is described above in the general context of program modules that execute in conjunction with an application program that runs on an operating system on a computer, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. Aspects of the invention may also be practiced in distributed computing environments where tasks are performed by remote processing devices that are linked through a communications network. In a distributed computing environment, program modules may be located in both local and remote memory storage devices.

FIG. 1 depicts an illustrative computer architecture for a computer 100 for practicing the various embodiments of the invention. The computer architecture shown in FIG. 1 illustrates a conventional computer, including a central processing unit 150 ("CPU"), a system memory 105, including a random-access memory 110 ("RAM") and a read-only memory ("ROM") 115, and a system bus 135 that couples the system memory 105 to the CPU 150. A basic input/output system containing the basic routines that help to transfer information between elements within the computer, such as during startup, is stored in the ROM 115. The computer 100 further includes a storage device 120 for storing an operating system 125, application/program 130, and data.

The storage device 120 is connected to the CPU 150 through a storage controller (not shown) connected to the bus 135. The storage device 120 and its associated computer-readable media provide non-volatile storage for the computer 100. Although the description of computer-readable media contained herein refers to a storage device, such as a hard disk or CD-ROM drive, it should be appreciated by those skilled in the art that computer-readable media can be any available media that can be accessed by the computer 100.

By way of example, and not to be limiting, computer-readable media may comprise computer storage media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

According to various embodiments of the invention, the computer 100 may operate in a networked environment using logical connections to remote computers through a network 140, such as TCP/IP network such as the Internet or an intranet. The computer 100 may connect to the network 140 through a network interface unit 145 connected to the bus 135. It should be appreciated that the network interface unit 145 may also be utilized to connect to other types of networks and remote computer systems.

The computer 100 may also include an input/output controller 155 for receiving and processing input from a number of input/output devices 160, including a keyboard, a mouse, a touchscreen, a camera, a microphone, a controller, a joystick, or other type of input device. Similarly, the input/output controller 155 may provide output to a display screen, a printer, a speaker, or other type of output device. The computer 100 can connect to the input/output device 160 via a wired connection including, but not limited to, fiber optic, Ethernet, or copper wire or wireless means including, but not limited to, Wi-Fi, Bluetooth, Near-Field Communication (NFC), infrared, or other suitable wired or wireless connections.

As mentioned briefly above, a number of program modules and data files may be stored in the storage device 120 and/or RAM 110 of the computer 100, including an operating system 125 suitable for controlling the operation of a networked computer. The storage device 120 and RAM 110 may also store one or more applications/programs 130. In particular, the storage device 120 and RAM 110 may store an application/program 130 for providing a variety of functionalities to a user. For instance, the application/program 130 may comprise many types of programs such as a word processing application, a spreadsheet application, a desktop publishing application, a database application, a gaming application, internet browsing application, electronic mail application, messaging application, and the like. According to an embodiment of the present invention, the application/program 130 comprises a multiple functionality software application for providing user interface, word processing functionality, slide presentation functionality, spreadsheet functionality, database functionality and the like.

The computer 100 in some embodiments can include a variety of sensors 165 for monitoring the environment surrounding and the environment internal to the computer 100. Additionally, computer 100 may include a variety of sensors 165 for monitoring a human subject. These sensors 165 can include a Global Positioning System (GPS) sensor, a photosensitive sensor, a gyroscope, a magnetometer, thermometer, a proximity sensor, an accelerometer, a microphone, biometric sensor, barometer, humidity sensor, radiation sensor, or any other suitable sensor. In some embodiments, computer 100 may connect to and control a pump for moving breathable air. In some embodiments, computer 100 may connect to and control a motor for moving breathable air. For example, computer 100 may connect to and control a vacuum pump and connect to and receive a signal from a pressure transducer, a manometer and a pneumotachograph, as further elaborated upon below.

Myofunctional Training with Negative Airway Pressure for Obstructive Sleep Apnea The present invention provides a system configured to provide negative airway pressure to a subject's airway. In one embodiment, the system of the present invention is configured to exercise the oropharynx and increase muscle tone. In one embodiment, the system of the present invention is configured to decrease upper airway collapsibility during sleep.

Figure 2:
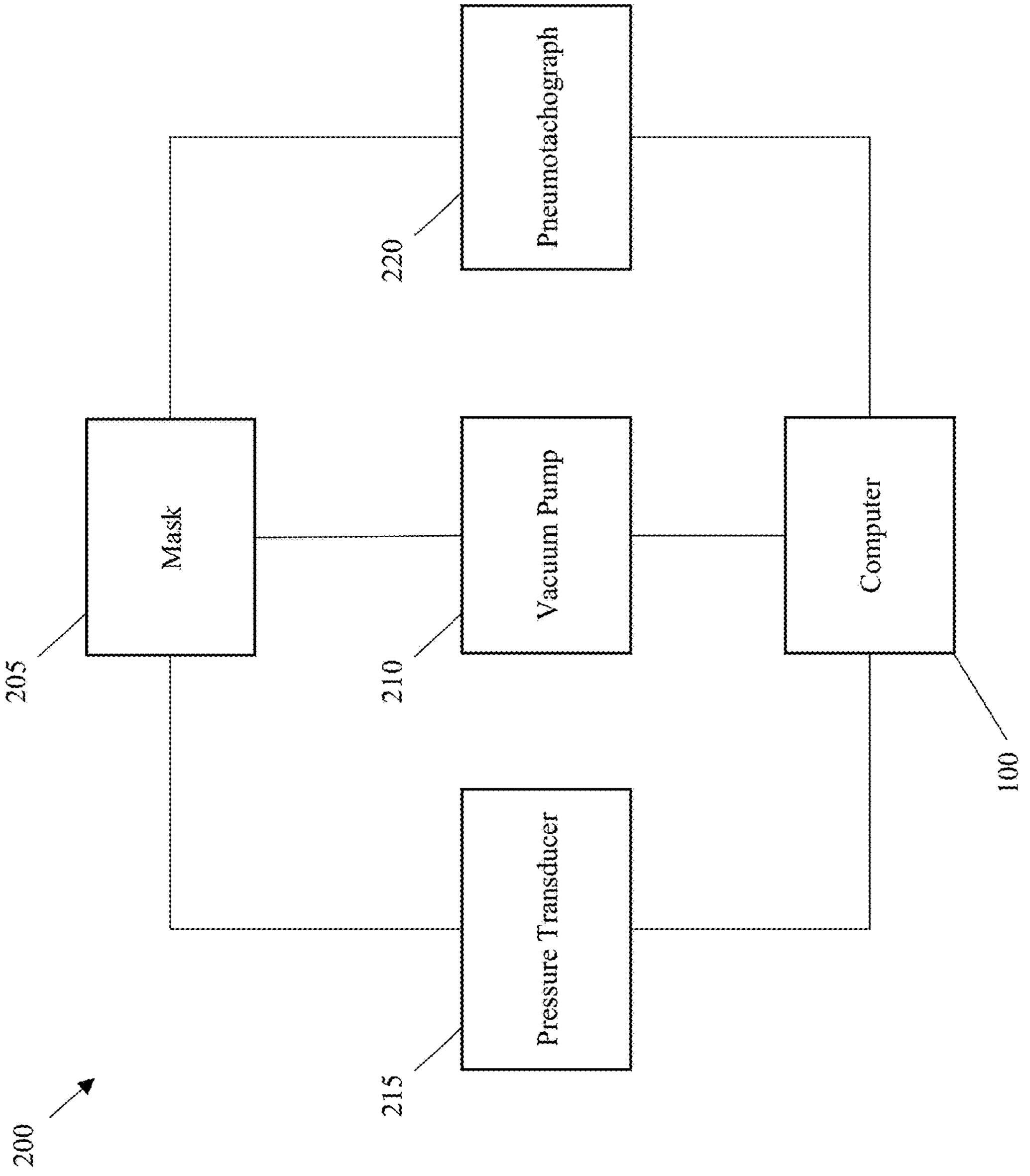
FIG. 2 is a diagram of a negative airway pressure system according to an aspect of the present invention.

Now referring to FIG. 2, shown is a system for providing negative airway pressure to a subject's airway comprising a mask, a vacuum pump, a pressure transducer, a pneumotachograph and a computer device. As shown, system 200 comprises mask 205 in fluid communication with vacuum pump 210, pressure transducer 215 and pneumotachograph 220. Further, system 200 comprises vacuum pump 210, pressure transducer 215 and pneumotachograph 220 connected to computer 100. In some embodiments, vacuum pump 210 is controlled by computer 100. In some embodiments, pressure transducer 215 and pneumotachograph 220 are connected to, and provide signals to computer 100.

In one embodiment, the system of the present invention comprises mask 205 configured to be placed over the subject's face. In one embodiment, mask 205 is configured to cover the subject's nasal and oral region. In one embodiment, mask 205 is sealingly placed over the subject's face and forms chamber between the mask and the subject's face. In one embodiment, mask 205 can have any shape known to one skilled in the art. In one embodiment, mask 205 can be made from any material known to one skilled in the art. In one embodiment, mask 205 may further comprise a securement member including but not limited to a strap, configured to hold the device in place. In one embodiment, mask 205 may be a commercial-off-the-shelf mask as would be known to one skilled in the art.

In one embodiment, the system of the present invention may comprise a mouthpiece configured to be placed over or inside the subject's mouth. In one embodiment, the mouthpiece may have any shape known to one skilled in the art. In one embodiment, the mouthpiece may be made from any material known to one skilled in the art. In one embodiment, the mouthpiece may further comprise a securement member including but not limited to a strap, configured to hold the device in place. In one embodiment, the mouthpiece may be a commercial-off-the-shelf mouthpiece as would be known to one skilled in the art.

In one embodiment, the system of the present invention further comprises vacuum pump 210, configured to provide a pressure of approximately between −1 to −25 cm $H_2O$ to the subject. In one embodiment, the vacuum pump may be able to provide a pressure of less than −25 cm $H_2O$ to the subject. In one embodiment, the vacuum pump may be able to provide a pressure of more than −1 cm $H_2O$ to the subject. In one embodiment, vacuum pump 210 is in fluid communication with mask 205 or a mouthpiece. In one embodiment, vacuum pump 210 is connected to mask 205 or a mouthpiece through an inlet port. In one embodiment, vacuum pump 210 may be attached to mask 205 or a mouthpiece by any means known to one skilled in the art. In one embodiment, vacuum pump 210 may be connected and controlled by computer 100.

In one embodiment, the device of the present invention may further comprise at least one sensor including but not limited to a pneumotachograph. In one embodiment, the at least one sensor may be positioned anywhere within mask 205 or system 200. In one embodiment, pneumotachograph 220 is positioned in fluid communication with vacuum pump 210 and mask 205 and measures a flow of air. In one embodiment, pneumotachograph is positioned to measure a flow of air from mask 205 to the subject. In one embodiment, pneumotachograph 220 is connected to computer 100 and reports a signal indicating the flow of air to or from mask 205. In one embodiment, pneumotachograph 220 is connected to computer 100 and measures the flow of air from mask 205 to the subject, or from the subject to mask 205.

In one embodiment, the device of the present invention may further comprise a pressure transducer configured to measure the pressure in a mask or a mouthpiece. In one embodiment, pressure transducer 215 is in fluid communication with mask 205. In one embodiment, pressure transducer 215 is in fluid communication with mask 205, vacuum pump 210 and pneumotachograph 220. In one embodiment, pressure transducer 215 may be connected to mask 205 or a mouthpiece by any means known to one skilled in the art. In one embodiment, pressure transducer 215 may be connected to mask 205 or the mouthpiece through a port. In one embodiment, the pressure within mask 205 or a mouthpiece may be calibrated with a manometer. In one embodiment, pressure transducer 215 measures the pressure within mask 205 and the pressure outside of mask 205. In one embodiment, the pressure transducer is connected to computer 100. In one embodiment, the manometer is connected to computer 100. In one embodiment, the pressure transducer and manometer are connected to computer 100.

In one aspect, the present invention provides a method for treating or improving the symptoms of a subject with obstructive sleep apnea (OSA). In one embodiment, the method of present invention is configured to exercise the oropharynx and increase muscle tone. In one embodiment, the method of the present invention is configured to decrease upper airway collapsibility during sleep. In one embodiment, the method of the present invention provides a method of upper airway muscle training for treating signs and symptoms of OSA.

In one embodiment, the method of the present invention comprises a step of measuring one-repetition maximum (1RM) of a subject. In one embodiment, 1RM is the unit designated to describe a maximum weight or resistance that a muscle group can move. In one embodiment, 1RM may be defined as the maximum negative pressure the participant could comfortably tolerate for one breath. In one embodiment, 1RM may be not less than −25 cm $H_2O$. In one embodiment, the method further comprises a step of delivering a negative airway pressure to the subject.

In one embodiment, negative airway pressure may be delivered based on the measured 1RM of the subject to the subject through any means known to one skilled in the art. For example, in certain embodiments, negative airway pressure may be delivered using a device or system of the invention, as described above. In one embodiment, negative airway pressure may be delivered to a subject through a mask. In one embodiment, the mask may be configured to cover the subject's nasal and oral region. In one embodiment, negative airway pressure may be delivered to a subject through a mouthpiece. In one embodiment, the negative airway pressure may be delivered repetitiously for 1-5 breaths per set. In one embodiment, the negative airway pressure may be delivered repetitiously for more than 5 breaths per set. In one embodiment, the negative airway pressure may be delivered between approximately 4-7 sets. In one embodiment, the negative airway pressure may be delivered for less than 4 sets. In one embodiment, the negative airway pressure may be delivered for more than 7 sets. In one embodiment, the method may further comprise a resting period of approximately 1-2 minutes between each set. In one embodiment, the resting period may be more than 2 minutes. In one embodiment, the resting period may be less than 1 minute.

In one embodiment, 1RM may be re-evaluated and adjusted periodically. In one embodiment, 1RM may be re-evaluated and adjusted after the first month. In one embodiment, 1RM may be re-evaluated and adjusted after the second month. In one embodiment, 1RM may be re-evaluated and adjusted anytime during the treatment period.

In one embodiment, the negative airway pressure may be delivered to the subject at least once a week. In one embodiment, the negative airway pressure may be delivered to the subject three times a week. In one embodiment, the negative airway pressure may be delivered to the subject any applicable times known to one skilled in the art. In one embodiment, the negative airway pressure may be delivered to the subject at least once a week for three months. In one embodiment, the negative airway pressure may be delivered three times a week for three months. In one embodiment, the negative airway pressure may be delivered for any period of time known to one skilled in the art.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples, therefore, specifically point out exemplary embodiments of the present invention, and are not to be construed as limiting in any way the remainder of the disclosure.

Example 1: Myofunctional Training with Negative Airway Pressure for Obstructive Sleep Apnea This study demonstrates the novel use of a modified standard PAP machine to provide negative airway pressure as a form of quantifiable myofunctional therapy for OSAS. In this small cohort, the intervention caused a decrease in AHI in some subjects. Overall, it was also shown that this intervention did not cause any harm.

The collapsibility of the upper airway during sedation-induced sleep has been studied by provoking its occurrence through the use of negative airway pressure (NAP) (Norton, J. R. et al., 2006, Anesthesiology 104:1155-1164; Litman R. S. et al., 2002, Anesthesiology 96:342-345). People who are awake can breathe against this negative airway pressure (it feels like a vacuum on the back of the throat) down to negative pressures that would readily collapse the airway during sleep or sedation. Awake and healthy OSA patients have been able to tolerate breathing with the application of up to −40 cm of water (Suratt, P. M. et al., 1984, J Appl Physiol Respir Environ Exerc Physiol 57:140-146). The ability to tolerate these pressures is the result of increased airway muscle tone (both tonic and reflex phasic activation of the airway dilator muscles) (Wheatley, J. R. et al., 1993, Am Rev Respir Dis 148:597-605).

Studied subjects in the lab have commonly described their breathing against this vacuum as a "workout" on their airway. Thus, the idea to test the ability of NAP application as a therapeutic intervention, exercising the oropharynx, increasing muscle tone and thus decreasing upper airway collapsibility during sleep was conceived, which is investigated herein. Over the last decade, orofacial myofunctional therapy (OMT) has been applied to treat this disorder (Guimaraes, K. C. et al., 2009, Am J Respir Crit Care Med 179:962-966). Both as a stand-alone therapy and in conjunction with PAP, OMT has been shown to reduce the apnea-hypopnea index, reduce snoring, and improve quality of sleep and life (Hsu, B. et al., 2020, J Clin Sleep Med 16:785-801). While other OMT protocols involve methods that require specific training (Guimaraes, K. C. et al., 2009, Am J Respir Crit Care Med 179:962-966; Neumannova, K. et al., 2018, Sleep Med 52:92-97; Puhan, M. A. et al., 2006, BMJ 332:266-270), it was considered that OSA sufferers already familiar with PAP would more easily adapt to the novel protocol described in the present application which involves the use of a similar device.

Though PAP therapy remains the gold standard approach for effective treatment of OSA (Mediano, O. et al., 2019, J Clin Med 8), compliance remains a challenge (Weaver, T. E. et al., 2008, Proc Am Thorac Soc 5:173-178). OMT has emerged as a promising alternative or adjunct to standard OSA therapy (Guimaraes, K. C. et al., 2009, Am J Respir Crit Care Med 179:962-966). In a recent review of the 11 studies published to date, de Felicio et al. provides an analysis of comparative methodology and ideas for further study (de Felicio C. M. et al., 2018, Nat Sci Sleep 10:271-286). In most OMT studies, the intervention exercises target a variety of oral and facial muscles including the tongue, palate, pharynx, mouth, and cheeks. In this study, the NAP therapy was hypothetically the reverse of PAP and may have exercised similar structures. However, it is not known whether NAP targets specific muscles whose tone (or lack thereof) contributes to OSA. With increasing attention being paid to OSA phenotypes, it has been suggested that most would benefit from anatomic intervention (Eckert, D. J. et al., 2013, Am J Respir Crit Care Med 188:996-1004). In addition, standardized classification of location, directionality and severity of pharyngeal collapse as determined during drug-induced sedation endoscopy (Kezirian, E. J. et al., 2011, Laryngoscope 121:1320-1326) could be explored as a method to target appropriate candidates who might benefit from myofunctional therapy, as it has been used to evaluate success with other OSA interventions such as surgery and electrical stimulation.

That prior familiarity with the PAP machine but failure to adhere to nighttime usage is a reasonable approach for recruitment of subjects for this study which included daytime and more limited use of the machine. In hindsight, non-use of PAP may have actually been an inappropriate criterion for inclusion as this may have predicted a phenotype á priori which would not benefit from this approach of myofunctional therapy (Eckert, D. J. et al., 2013, Am J Respir Crit Care Med 188:996-1004). Most PAP machines can now be interrogated to ensure patient compliance. Future investigations may benefit from recruiting PAP users and assessing devices for pressure changes over the course of an exercise intervention during wakefulness.

As was done in this study, OMT is typically utilized during wakefulness as a method to decrease muscle hypotonia during sleep. Theoretically, the frequent repetitions at low levels of resistance may target Type 1 (slow-resistant to fatigue) muscles, such as those found in the tongue (Clark, H. M. et al., 2003, Am J Speech Lang Pathol 12:400-415). These muscles and Type 2A (fast-intermediate fatigue) muscles have been stimulated electrically (Mann, E. A. et al., 2002, Laryngoscope 112:351-356; Smith, P. L. et al., 1996, Sleep 19:S284-287) and trained (Puhan, M. A. et al., 2006, BMJ 332:266-270; Laqueux, T. et al., 2005, Eur Arch Otorhinolaryngol 262:501-503). In patients with OSA there are even more type 2A fibers than in normal controls, which could contribute to the increase fatigability (Series, F. et al., 1996, FASEB J 10:897-904).

This protocol lasted for three months, a time period that is frequently used in muscle training (de Felicio, C. M. et al., 2018, Nat Sci Sleep 10:271-286). Unlike other protocols, it was chosen to have subjects observed in a laboratory and reasoned that visiting three times per week would not be too onerous. Many of the training protocols describe daily exercises, sometimes three (Guimaraes, K. C. et al., 2009, Am J Respir Crit Care Med 179:962-966; Diaferia, G. et al., 2017, Sleep Breath 21:387-395) to five times (Verma, R. K. et al., 2016, Sleep Breath 20:1193-1202) per day. It is possible that this training regimen was not sufficient to see an effect.

Subjects were asked to maintain a mouth closed position while performing exercises, mostly as a means to standardize their positions. It has also been shown that mouth breathing exacerbates upper airway obstruction with advocates for mouth closure training to promote airway patency maintenance during sleep (Catlin, G. et al., Paternoster ROW: N. Truebner & Co. 1870; Suzuki, H. et al., 2013, J Prosthodont Res 57:195-199).

Despite the limitations of this study, there were no reported adverse events. In contrast, participants shared that they appreciated doing this therapy, and could envision doing it at home were it to become available.

The materials and methods are now described.

Twenty subjects (>18 years of age) were screened and 15 recruited for the study. All subjects had a diagnosis of OSA (Apnea Hypopnea Index, AHI>10) but were not currently using their previously prescribed PAP. Each participant received a targeted history and physical exam to assess for stability of medical conditions, including having a normal electrocardiogram, and a negative urine drug test. Measurements of body mass index (BMI), neck circumference, and an airway exam were collected, and the Epworth sleepiness scale survey was administered. Exclusion criteria included: major upper airway morphologic abnormality (such as profound micrognathia), history of airway surgery, regular use of central nervous system depressants or alcohol (e.g., >14 alcoholic drinks per week or >2 per day), morbid obesity ($BMI \geq 40$ kg/m$^2$), (Suratt, P. M. et al., 1984, J Appl Physiol Respir Environ Exerc Physiol 57:140-146) or unstable medical or psychiatric illness. Participants were also excluded if they were undergoing or planning to undergo an intervention for weight loss, or pregnant or lactating. All subjects provided written informed consent.

Participants were initially evaluated with an overnight polysomnographic study incorporating 16 electrophysiologic signals: 2-channel electro-oculogram, 8-channel electroencephalogram (Fz, C3, CZ, C4, Pz, Oz, T3, and T4), bipolar mentalis electromyogram, 2 lead electrocardiogram, nasal/oral airflow thermocouple, two respiratory effort sensors, a pulse oximeter, and a channel representing A1/A2. The resulting data were analyzed in 30-second epochs by an independent and certified sleep scorer.

Training Visits

The NAP myofunctional therapy protocol was designed to minimize the development of muscle hypertrophy and optimize strength and/or endurance (Bird, S. P. et al., 2005, Sports Med 35:841-851). In muscle conditioning therapy, one-repetition maximum (1RM) is the unit designated to describe a maximum weight or resistance that a muscle group can move. For this study, the 1RM was defined as the maximum negative pressure the participant could comfortably tolerate for one breath, not less than −25 cm $H_2O$. As is conventional in exercise physiology, ideal strength training involves targeting each subject's 1RM repetitiously for 1-5 breaths per set and repeating this set 4-7 times with rests of 1-2 minutes between sets.

The initial visit to the outpatient clinical research center was used to familiarize subjects with the apparatus which appears similar to a typical PAP machine. Subjects were acclimated to both the mask fit (over the mouth and nose) and the feeling of breathing against a negative pressure. Airflow was measured with a pneumotachograph (Hans Rudolph, Shawnee, KS) inserted into the mask which was calibrated with a rotameter. Mask pressure was measured by connecting a port to a pressure transducer (Validyne, Northridge, CA) calibrated with a water manometer.

Subjects were instructed to breathe through the nose with a closed mouth while sitting in order to minimize any tendency for the upper airway to collapse. At the first visit, the participants were exposed to a variety of negative pressures in an increasing-decreasing manner (from −5 cm $H_2O$ for five breaths and down) and also in random sequence in order to determine each subject's 1RM.

Thereafter, the subjects would schedule three observed sessions per week for three months in the clinical research center. As described above, each session entailed the subject breathing NAP at the predefined 1RM for five breaths per set (reps), and repeating this set 4-7 times with rests of 1-2 minutes between sets. Constant observation by study personnel allowed for verification of wakefulness (eyes open) and breathing with the mouth closed during the entire procedure. Each session lasted approximately 30 minutes. After the first and second month, the 1RM was re-evaluated and adjusted, as appropriate. For the following month, the new 1RM of NAP was used for the training exercises. Each subject's BMI and neck circumference were re-measured after the first and second months.

Participants completed a post-intervention overnight sleep study within a week of finishing the prescribed course of airway physical therapy. Data from this study were collected and analyzed in the same manner as the initial overnight sleep study.

Participants were also instructed to maintain nightly sleep diaries. This included recording and rating aspects of sleep quality and sleep-related quality of life on a 1-5 scale upon waking and recording bedtimes, time out of bed, time required to fall asleep, number of awakenings during the night, time awake after falling asleep, time awake before alarm or intended wake time, and time out of bed at night.

Outcome Measures

Since this was a pilot study without a control group, the primary outcome was a difference in AHI (as measured by overnight attended polysomnography) between the initial sleep study and the final study in each subject. Specifically, the study was sized to detect a 50% reduction in AHI or an AHI reduction of more than 10. Other secondary outcomes include nadir saturation, non-REM AHI, and protocol compliance. A pre-planned subgroup analysis of the subjects with a mild to moderate AHI (AHI<30) was performed.

Statistical Analysis

For the primary analysis, the differences between baseline and post-intervention data were analyzed using paired student's t-tests. Symptoms scores were analyzed nonparametrically.

Data are reported as mean t standard deviation and 95% confidence intervals. $p \leq 0.05$ was considered significant. All statistical analyses were performed using STATA/IC 13.1, (Stata Corp LP, College Station, TX).

The results are now described.

Figure 3:
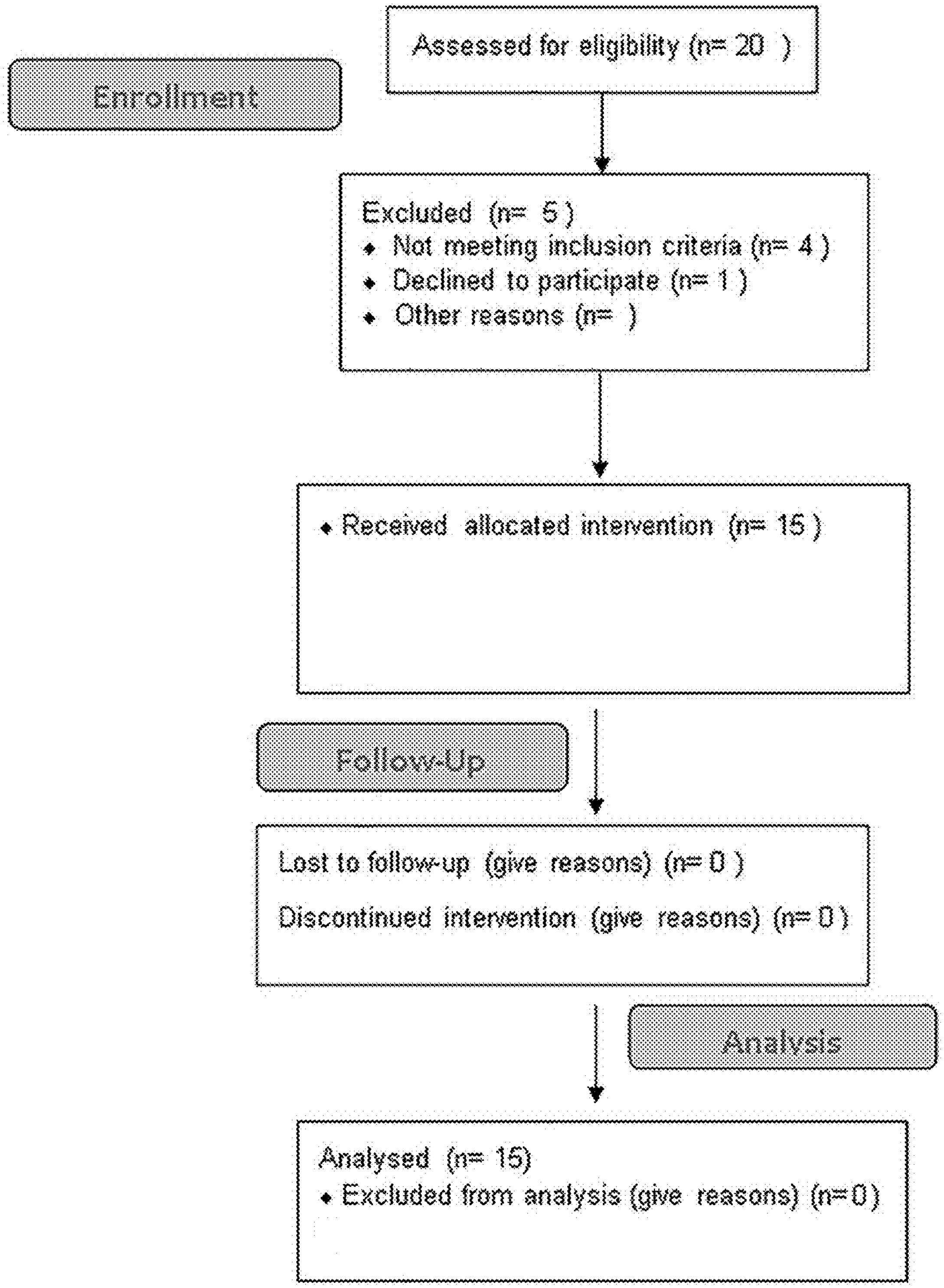
FIG. 3 is a CONSORT (Consolidated Standards of Reporting Trials) flow diagram.

Fifteen subjects completed the study and Table 1 provides their demographics which demonstrates no significant changes in BMI, weight or neck circumference after the training sessions (see FIG. 3 for CONSORT flow chart). The initial airway training pressures ranged from −8 to −18 cm $H_2O$ and all airway training pressures became more negative except for one subject who stayed at −18 cm $H_2O$ (FIG. 4) which was the most extreme pressure utilized for the study.

TABLE 1

Subject characteristics for all subjects N = 15, unless noted) and the pre-planned subgroup of subjects with an AHI < 30 (N = 8 unless noted). BMI = body mass index. Data is mean ± standard deviation.

| | Pre-study | Post-study |
|---|---|---|
| All subjects (N = 15) | | |
| Age (years) | 57.8 ± 13.3 | |
| BMI (kg/m$^2$) | 32.8 ± 6.3 | 32.8 ± 5.7 |
| Weight (kg) | 97 7 ± 22.9 (N = 14) | 100.1 ± 22.5 |
| Neck Circumference (cm) | 17.1 ± 2.3 | 16.9 ± 2.0 (N = 13) |
| Mild/Moderate Pre-study AHI (AHI < 30); N = 8 | | |
| Age (years) | 64.4 ± 6.22 | |
| BMI (kg/m$^2$) | 30.6 ± 5.7 | 31.0 ± 5.2 |
| Weight (kg) | 93.5 ± 24.2 | 94.3 ± 27.6 |
| Neck Circumference (cm) | 16.5 ± 2.0 | 16.4 ± 1.6 (N = 7) |

Figure 4:
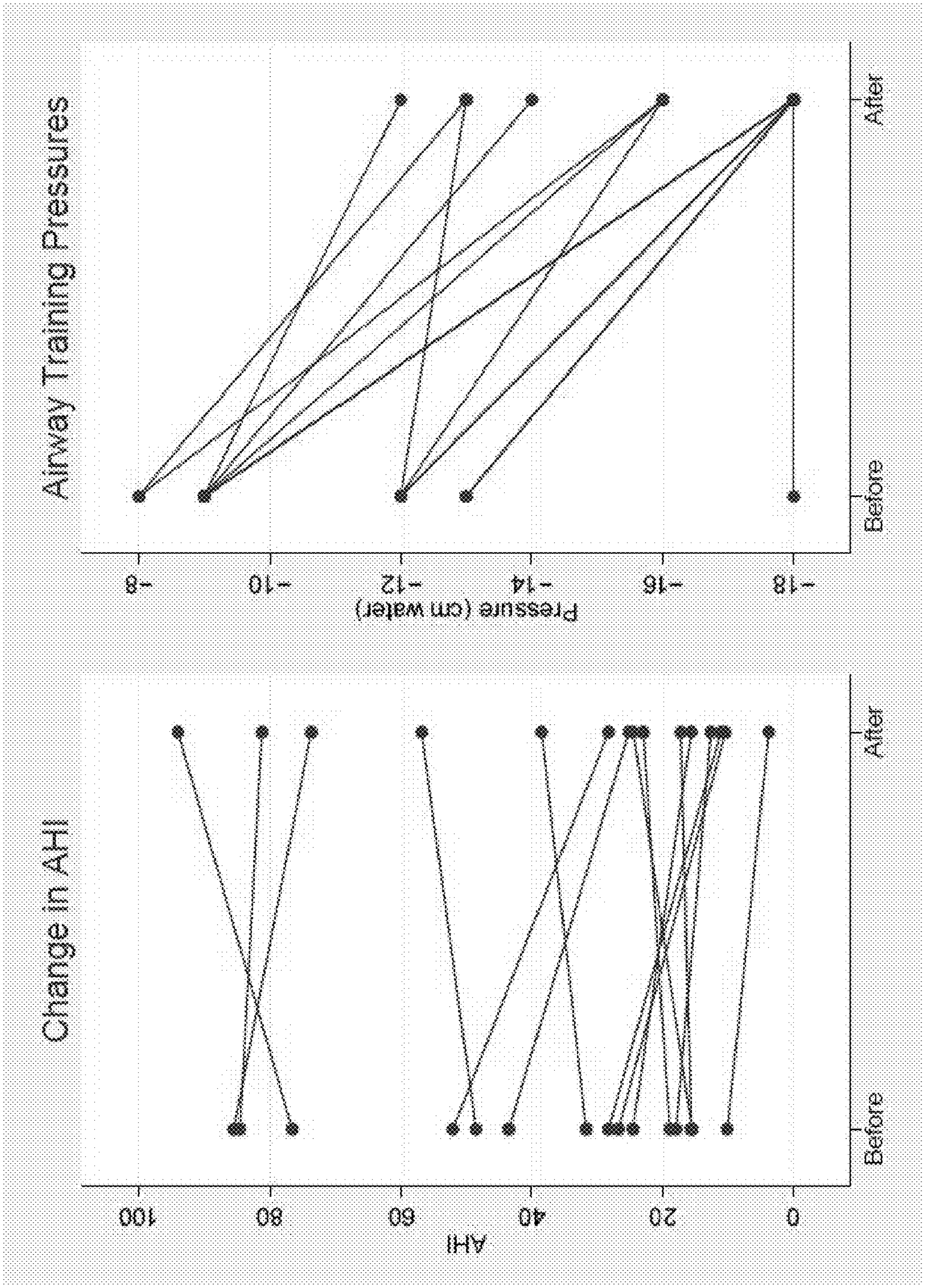
FIG. 4 depicts changes to the apnea hypopnea index (AHI) and training pressure from before and after the training for all subjects. The left panel shows the change in the AHI from before and after the training for all subjects. The right panel shows the change in the initial to the final training pressure.

While the mean post study AHI was slightly improved (−4.3±12.0 [−10.9, 2.3]), it was not statistically significant (Table 2). Six subjects actually increased their AHI, only one subject decreased to below 10 and this was the subject with the lowest pre-study AHI of 10.1 (FIG. 4). The results were similar when the AHI was categorized by the sleep state (REM vs. non-REM). The nadir saturation was also essentially unchanged. The eight subjects with mild or moderate OSA (AHI<30) showed similar results.

TABLE 2

Ventilatory outcomes from the overnight polysomnographic studies before (pre-study) and after (post-study) the airway strength training intervention for both the full group and the mild/moderate AHI subgroup. AHI-apnea hypopnea index. The AHI was calculated during rapid eye movement (REM) and non-REM sleep. Data given as mean ± stand deviation, except for difference which is mean and 95% confidence interval.

| | Pre-study | Post-study | Difference (95% CI) |
|---|---|---|---|
| All subjects (N = 15) | | | |
| AHI | 38 7 ± 25.7 | 34.4 ± 28.5 | −4.3 (−10.9, 2.3) |
| Nadir Sat (%) | 76.2 ± 18.2 | 77.6 ± 17.3 | 1.4 (−2.4, 5.2) |
| AHI (REM) | 41.6 ± 24.6 | 38.5 ± 26.8 | −3.1 (−16.7, 10.5) |
| AHI (non-REM) | 36.8 ± 28.0 | 33.6 ± 29.6 | −3.3 (−9.5, 3.0) |
| Mild/Moderate Pre-study AHI (AHI < 30); N = 8 | | | |
| AHI | 19.7 ± 6.3 | 14.8 ± 6.8 | −4.9 (−12.8, 2.9) |
| Nadir Sat (%) | 84.1 ± 7.3 | 83.6 ± 4.6 | −0.5 (−7.5, 6.5) |
| AHI (REM) | 27.8 ± 19.5 | 24.5 ± 13.3 | −3.3 (−25.3, 18.6) |
| AHI (Non-REM) | 15.9 ± 8.7 | 12.7 ± 7.8 | −3.2 (−11.3, 4.8) |

Of the 15 subjects, only 10 completed their sleep diaries. There were no differences noted in sleep quality or feeling refreshed from the intervention.

In conclusion, subjects with OSAS were able to tolerate a three-month exercise protocol using the novel application of negative airway pressure as orofacial myofunctional therapy. Though was no significant reduction in AHI in this small cohort, the methods elucidate a new daytime use for a machine with which many OSAS sufferers are familiar. Future studies utilizing this protocol may target current PAP users or those whose drug-induced sedation endoscopies indicate this approach as an alternative therapy.

The disclosures of each and every patent, patent application, and publication cited herein are hereby each incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A system comprising:

a mask to be placed sealingly over a subject's face and thereby form a chamber between the mask and the subject's face, wherein the mask comprises an inlet port configured to receive a flow of breathable gas;

a vacuum pump attached to one end of the inlet port, wherein the vacuum pump is capable of creating a pressure of about −1 to −25 cm $H_2O$ in the chamber; and a computing device connected to and configured to control the vacuum pump, comprising a non-transitory computer-readable medium with instructions stored thereon, which when executed by a processor, perform steps comprising:

activating the vacuum pump to provide a set of random negative pressures within the chamber;

calculating a one-repetition maximum (1RM) of a subject across the random negative pressures; and activating the vacuum pump to provide a target negative pressure within the chamber based on the 1RM.

2. The system of claim 1, wherein the mask is structured to cover the subject's nasal and oral region.

3. The system of claim 1, wherein the mask further comprises a pneumotachograph to measure air flow within the chamber.

4. The system of claim 1, wherein the mask further comprises a pressure transducer configured to measure the pressure in the mask.

5. A method for treating obstructive sleep apnea, comprising the steps of:

measuring one-repetition maximum (1RM) of a subject, wherein the 1RM is measured by exposing the subject to a variety of negative pressures in a random sequence; and providing negative airway pressure based on the measured 1RM to the subject.

6. The method of claim 5, wherein the negative airway pressure is provided to the subject through a mask sealingly positioned on the subject's face.

7. The method of claim 5, wherein the negative airway pressure is provided to the subject through a mouthpiece.

8. The method of claim 5, wherein the negative airway pressure is provided for approximately 4-7 sets wherein in each set, the subject is exposed to the measured 1RM repetitiously for at least 1 breath.

9. The method of claim 8, wherein the subject is exposed to the measured 1RM repetitiously for approximately 1-5 breaths.

10. The method of claim 8, wherein the subject is subjected to a rest time of at least 1 minutes between sets.

11. The method of claim 5, wherein the negative airway pressure is configured to be approximately about −1 to −25 cm $H_2O$.

* * * * *